US006418345B1

(12) United States Patent
Tepper et al.

(10) Patent No.: US 6,418,345 B1
(45) Date of Patent: Jul. 9, 2002

(54) PEMF STIMULATOR FOR TREATING OSTEOPOROSIS AND STIMULATING TISSUE GROWTH

(75) Inventors: John C. Tepper, Carrollton; Peter Kuo, Richardson; Kathy L. McDermott, Dallas, all of TX (US)

(73) Assignee: AMEI Technologies Inc., Wilmington, DE (US)

( * ) Notice: Subject to any disclaimer, the term of this patent is extended or adjusted under 35 U.S.C. 154(b) by 0 days.

(21) Appl. No.: 09/365,157

(22) Filed: Jul. 30, 1999

Related U.S. Application Data

(60) Provisional application No. 60/095,185, filed on Aug. 3, 1998.

(51) Int. Cl.$^7$ ................................................ A61N 2/02
(52) U.S. Cl. ............................ 607/51; 600/14; 600/15
(58) Field of Search ........................... 607/1–3, 50, 51, 607/115, 138, 148, 152, 154–156; 600/9, 13–15

(56) References Cited

U.S. PATENT DOCUMENTS

| 4,266,532 A | 5/1981 | Ryaby et al. |
| 4,456,001 A | 6/1984 | Pescatore |
| 4,501,265 A | 2/1985 | Pescatore |
| 4,548,208 A | 10/1985 | Niemi |
| 4,550,714 A | 11/1985 | Talish et al. |
| 4,561,426 A | 12/1985 | Stewart |
| 4,616,629 A | 10/1986 | Moore |
| 4,635,643 A | 1/1987 | Brown |

(List continued on next page.)

FOREIGN PATENT DOCUMENTS

| DE | 9 300 499 | 3/1993 | ............ A47C/9/02 |
| EP | 0 788 813 | 8/1997 | ............ A61N/2/02 |
| EP | 0 850 665 | 7/1998 | ............ A61N/2/02 |
| GB | 2 242 362 A | 10/1991 | |
| WO | 8 500 293 | 1/1985 | ............ A61N/1/40 |
| WO | 9 300 131 | 1/1993 | ............ A61N/1/40 |

OTHER PUBLICATIONS

English Translation of German Patent entitled *Seat for Magnethotherapy Application*, (previously cited on PTO–01449 filed Mar. 10, 2000) as 9 300 499 dated Mar. 25, 1993.

Bassett, C. Andrew L., "Fundamental and Practical Aspects of Therapeutic Uses of Pulsed Electromagnetic Fields (PEMFs)", *Critical Reviews in Biomedical Engineering*, vol. 17, Issue 5, pp. 451–529, 1989.

Cruess, R.L., K. Kan, and C.A.L. Bassett, "The Effect of Pulsing Electromagnetic Fields on Bone Metabolism in Experimental Disuse Osteoporosis", *Clinical Orthopaedics and Related Research*, No. 173, pp. 245–250, Mar., 1983.

Sherry, T. M., M. J. Pead, and L. E. Lanyon, "Modulation of Bone Loss During Disuse by Pulsed Electromagnetic Fields", *Journal of Orthopaedic Research*, vol. 9, No. 4, pp. 600–608, 1991.

Tabrah, Frank, Mary Hoffmeier, Fred Gilbert, Jr., Stanley Batkin, and C.A.L. Bassett, "Bone Density Changes in Osteoporosis–Prone Women Exposed to Pulsed Electromagnetic Fields (PEMFs)", *Journal of Bone and Mineral Research*, vol. 5, pp. 437–442, Nov. 5, 1990.

(List continued on next page.)

*Primary Examiner*—George R. Evanisko
(74) *Attorney, Agent, or Firm*—Baker Botts L.L.P.

(57) ABSTRACT

Apparatus and method for providing PEMF therapy to selected portions of a patient's body such as the hips and spine. The apparatus preferably includes at least two transducer coils. Electronics for driving the coils are contained in a housing. The housing is preferably connected to the transducer coil by a flexible cable. The housing preferably includes a battery power supply.

30 Claims, 6 Drawing Sheets

U.S. PATENT DOCUMENTS

| | | |
|---|---|---|
| 4,654,574 A | 3/1987 | Thaler |
| 4,662,378 A | 5/1987 | Thomis |
| 4,911,686 A | 3/1990 | Thaler |
| 4,932,951 A | 6/1990 | Liboff et al. |
| 4,974,114 A | 11/1990 | Kammerer |
| 5,058,582 A | 10/1991 | Thaler |
| 5,066,272 A | 11/1991 | Eaton et al. |
| 5,084,003 A * | 1/1992 | Susic .......................... 600/13 |
| 5,088,976 A | 2/1992 | Liboff et al. |
| 5,181,902 A | 1/1993 | Erickson et al. |
| 5,195,941 A * | 3/1993 | Erickson et al. .............. 600/14 |
| 5,269,747 A | 12/1993 | Erickson |
| 5,314,401 A | 5/1994 | Tepper |
| 5,318,561 A | 6/1994 | McLeod et al. |
| 5,338,286 A | 8/1994 | Abbott et al. |
| 5,351,389 A | 10/1994 | Erickson et al. |
| 5,401,233 A | 3/1995 | Erickson et al. |
| 5,478,303 A | 12/1995 | Foley-Nolan et al. |
| 5,518,496 A | 5/1996 | McLeod et al. |
| 5,743,844 A | 4/1998 | Tepper et al. |

OTHER PUBLICATIONS

Jacobson–Kram David, et al., "Evaluation of Potential Genotoxicity of Pulsed Electric and Electromagnetic Fields Used for Bone Growth Stimulation", *Elsevier Science B.V.*, pp. 45–57, 1997.

Glazer, Paul A., et al., Use of Electromagnetic Fields in a Spinal Fusion A Rabbit Model, *Spine An International Journal for the Study of the Spine*, vol. 22, No. 20, pp. 2351–2356, Oct. 15, 1997.

International Search Report for PCT/US99/1722, Nov. 23, 1999.

* cited by examiner

FIG. 5
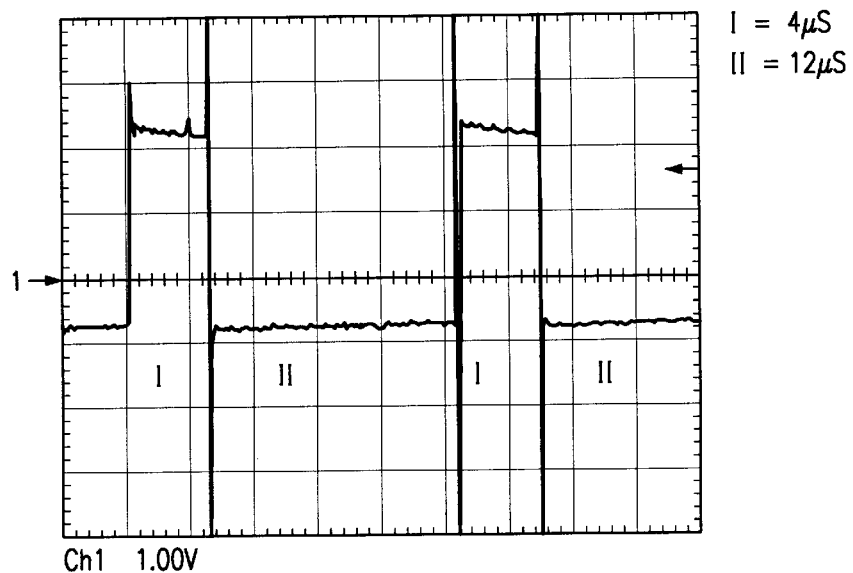
I = 4μS
II = 12μS
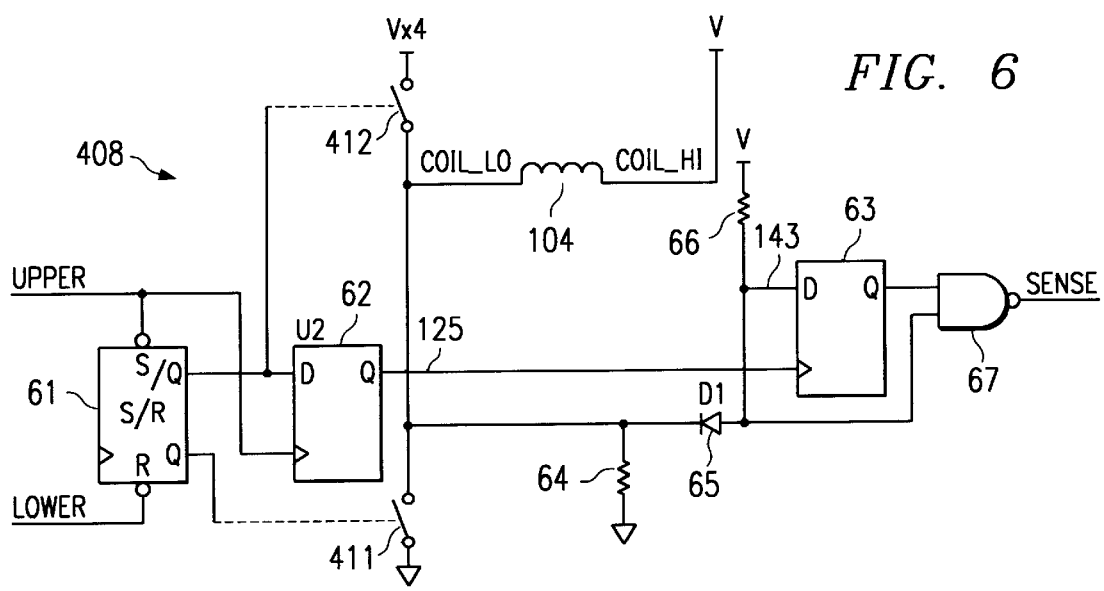
FIG. 6
FIG. 8
| PARAMETER | SYMBOL | REQUIREMENT | UNITS |
|---|---|---|---|
| BURST INTERVAL | Tbi | 667 ± 3 | ms |
| FIRST PULSE WIDTH (+) | tpwf (+) | 2 | μs |
| PULSE WIDTH (+) | tpw (+) | 4 | μs |
| PULSE WIDTH (−) | tpw (−) | 12 | μs |
| PULSES PER BURST | Np | 1609 | − |

PEMF STIMULATOR FOR TREATING OSTEOPOROSIS AND STIMULATING TISSUE GROWTH

RELATED PATENT APPLICATIONS

This application claims the benefit of U.S. Provisional Application Ser. No. 60/095,185 filed Aug. 3, 1998 entitled PEMF Stimulator for Treating Osteoporosis and Stimulating Tissue Growth.

This application is related to U.S. patent application Ser. No. 09/033,032 now U.S. Pat. No. 6,132,362 and Ser. No. 09/033,045, entitled "Pulsed Electromagnetic Field (PEMF) Stimulation Therapy System with Bi-Phasic Coil," and "Flexible Coil Pulsed Electromagnetic Field (PEMF) Stimulation Therapy System," filed Mar. 2, 1998. Both applications are continuations-in-part of U.S. Pat. No. 5,743,844, filed Nov. 1, 1996 by John C. Tepper, et. al., and entitled "High Efficiency Pulsed Electromagnetic Field (PEMF) Stimulation Therapy Method and System".

TECHNICAL FIELD OF THE INVENTION

The present invention relates generally to a PEMF stimulator for treating osteoporosis and other medical conditions by promoting an increased bone mineral content and density.

BACKGROUND OF THE INVENTION

Therapeutically difficult problems of the musculoskeletal system include spinal fusion, un-united fractures (or non-union fractures), failed arthrodeses, osteonecrosis, and chronic refractory tendinitis, decubitus ulcers and ligament, tendon injuries, osteoporosis, and Charcot foot. Such problems, especially fractures, may result from losses in bone mineral density. Osteoporosis in particular is responsible for 1.5 million fractures in the U.S. annually, especially hip, vertebral and wrist fractures. One conventional approach for treating such fractures is pharmaceutical therapy. This approach is disadvantageous because such therapy is generally expensive, and lasts for a patient's lifetime. Furthermore, such therapy may be associated with side effects which some patients may not tolerate.

Pulsed electromagnetic fields (PEMF) are low-energy, time-varying magnetic fields that are useful for treating such problems of the musculoskeletal system. For PEMF therapy, an electromagnetic transducer coil is typically placed in the vicinity of the fracture or fusion such that pulsing the electromagnetic transducer will produce an applied field that penetrates to the underlying bone.

One conventional approach is to use a flat oval-shaped transducer coil for PEMF fracture therapy. This approach is disadvantageous because the transducer coil may not cover the entire treatment area and the applied field has limited penetration. A second, coil design for spinal fusion incorporated both a primary coil and a secondary coil to provide broad field coverage inside a defined treatment volume. Accordingly, providing effective PEMF fracture therapy using a flat coil design with broad field coverage and good field penetration required a new coil and drive circuit design which permits the use of only a single, more compact and energy efficient coil. This design is described in detail in U.S. Pat. No. 5,743,844, entitled High Efficiency Pulsed Electromagnetic Field (PEMF) Stimulation Therapy Method and System.

SUMMARY OF THE INVENTION

In accordance with the teachings of the present invention, disadvantages and problems associated with the use of conventional flat or oval shaped coils or utilization of both a primary and secondary coil design have been substantially reduced or eliminated.

One aspect of the present invention includes a bone mineral density (BMD) stimulator for osteoporotic patients. The stimulator for this embodiment may sometimes be referred to as a PEMF stimulator or Osteoporosis stimulator. The stimulator generates a pulsed electromagnetic field (PEMF) which induces voltages and current to provide non-invasive treatment to increase bone mineral density (BMD). The pulsed electromagnetic field generated by the bone mineral density stimulator, provides a non-invasive treatment for osteoporosis. The signal is preferably of a similar frequency as that delivered by commercially available stimulators which have been clinically demonstrated to affect bone formation. The signal offers greater energy efficiency than many current commercial PEMF devices.

A flat coil design with broad field coverage and good field penetration permits the use of only a single coil, and results in a compact and more energy efficient coil to produce such a pulsed electromagnetic field, as is described in U.S. Pat. No. 5,743,844. Use of such a design can be advantageous in treating many areas at high risk for fractures due to osteoporosis. Such areas include, but are not limited to, the thoracic and lumbar spine, femoral head, neck, and the upper and lower extremities. At least two such coils may be disposed in a pad in at least one layer of elastomeric material. For some applications, the pad may include a polymeric material that may be deformed to assume various configurations and/or to provide support. For additional applications, an additional coil may be disposed in an extremity pad.

Technical advantages of the present invention include using PEMF therapy to increase bone density to a level that substantially decreases a patient's risk of fracture. For example, treatment over a broad field that would encompass all areas of bone particularly prone to osteoporotic fracture, including but not limited to areas such as the hip, spine and wrists, would be beneficial in increasing bone mineral density and/or content, thereby preventing osteoporotic fracture. Another technical advantage includes a synergistic effect when PEMF therapy is used in combination with pharmaceutical therapy. Yet another technical advantage includes using PEMF therapy to provide a patient a single daily treatment to simultaneously treat areas subject to fracture. The cost of such PEMF therapy is substantially reduced as compared to the cost associated with pharmaceutical treatment of osteoporosis. Such PEMF therapy may provide a suitable replacement therapy for patients who cannot be treated with pharmaceuticals. A bone mineral density stimulator incorporating teachings of the present invention may be used for prevention of hip, spinal, wrist and/or other fractures.

Further technical advantages of the present invention include producing an energy efficient PEMF signal with a pulse period between ten microseconds (10 $\mu$sec) and twenty microseconds (20 $\mu$sec). For some applications, a bone mineral density stimulator producing a PEMF signal with a pulse period of approximately sixteen microseconds (16 $\mu$sec) will be very energy efficient.

BRIEF DESCRIPTION OF THE DRAWINGS

For a more complete understanding of the present invention, and the advantages thereof, reference is now made to the following brief descriptions, taken in conjunction with the accompanying drawings and detailed description, wherein like reference numerals represent like parts, in which:

FIG. 5 is a drawing showing a typical wave form generated by the transducer coils shown in FIGS. 1A and 4;

FIG. 6 is a schematic drawing showing the coil break detector circuit of FIG. 4;

FIG. 8 is a table of drive signal parameters corresponding with one embodiment of the present invention as represented by the diagrams of FIGS. 6 and 7;

DETAILED DESCRIPTION OF THE INVENTION

The preferred embodiments of the present invention and its advantages are best understood by referring now in more detail to FIGS. 1A–10C of the drawings, in which like numerals refer to like parts.

Figure 1A:
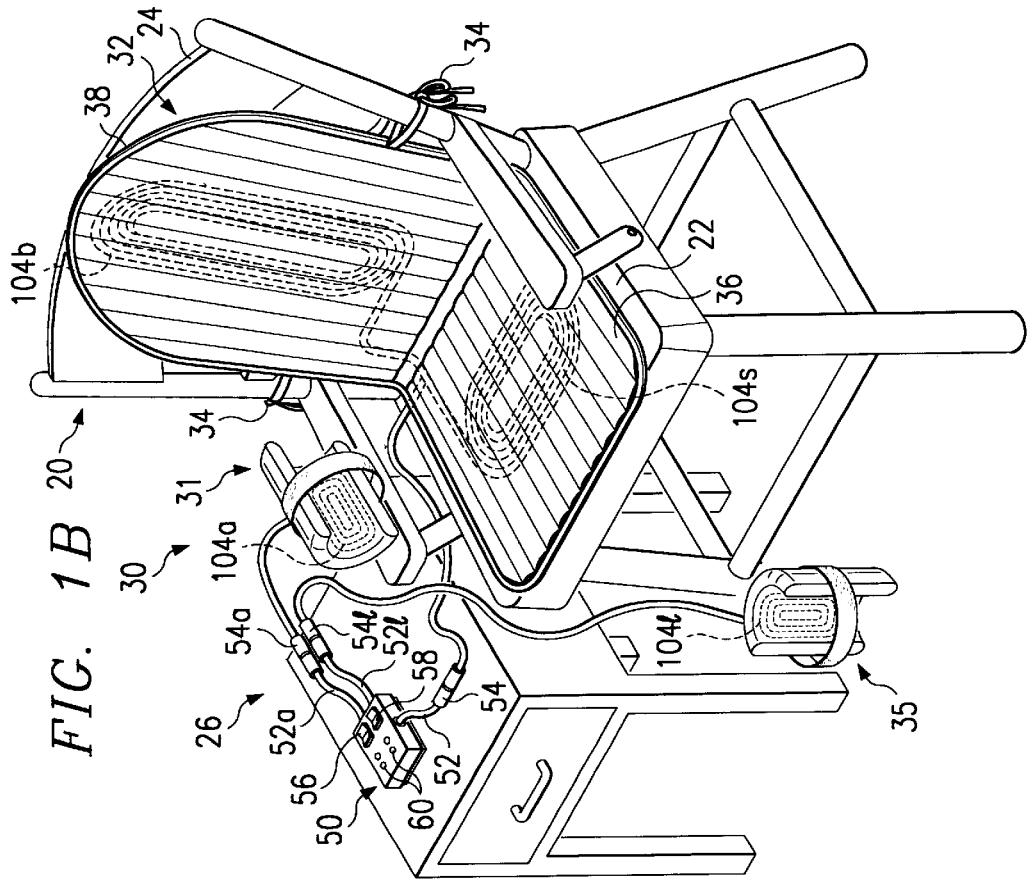
FIG. 1A is a schematic drawing showing an isometric view of a bone mineral density stimulator incorporating teachings of the present invention disposed on a chair for treatment of a patient with electromagnetic therapy.

Bone mineral density stimulator 30 incorporating teachings of the present invention is shown in FIG. 1A secured to chair 20. Bone mineral density stimulator 30 produces electrical signals similar to Spinal-Stim® Lite devices that are offered by Orthofix. In operation, bone mineral density stimulator 30 includes a control unit or housing 50 sending a programmed signal to at least two transducer coils 104s and 104b. The PEMF signal generated by bone mineral density stimulator 30 may consist of a burst of one thousand six hundred nine (1609) pulses, at a repetition rate of one and one-half (1.5) pulse bursts per second. Each individual pulse consists of a positive (energization) portion, four microseconds (4 μsec) wide, and a negative (de-energization) portion, approximately twelve microseconds wide (12 μsec). The amplitude of the positive portion is about three times the amplitude of the negative portion. Bone mineral density stimulator 30 is designed to provide a uniform magnetic field and constant peak flux densities throughout the volume of the treatment site.

Figure 2:
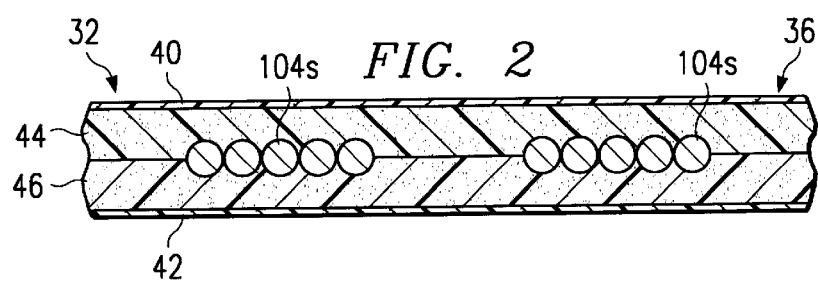
FIG. 2 is a schematic drawing in section with portions taken along lines 2—2 of FIG. 1A showing a portion of a first transducer coil.
Figure 3:
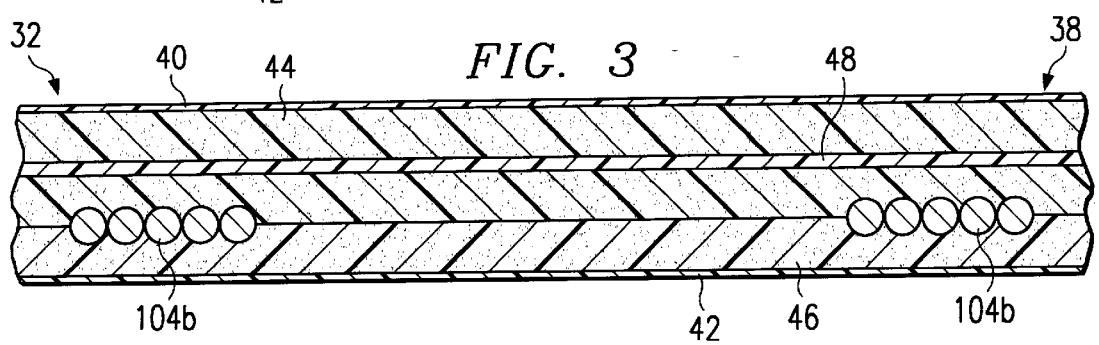
FIG. 3 is a schematic drawing in section with portions taken along lines 3—3 of FIG. 1A showing portions of a second transducer coil.

For the embodiment of the present invention as shown in FIGS. 1A, 2 and 3, bone mineral density stimulator 30 includes pad 32 and control unit or housing 50. Pad 32 preferably includes first portion 36 having a configuration corresponding with seat 22 of chair 20 and second portion 38 having a general configuration corresponding with back 24 of chair 20. For the embodiment as shown in FIG. 1A, pad 32 may have an approximate length of forty-four inches (44") and width of approximately twenty-one inches (21"). First portion 36 may be flexibly coupled to second portion 38.

In this embodiment, pad 32 is releasably secured to chair 20 by flexible straps 34. Pad 32 may be releasably secured to chair 20 in other embodiments by other suitable means (not expressly shown) located at any suitable location on pad 32. Such securing means include, but are not limited to, additional straps 34, an elastic slip cover, or straps that secure with buckles or Velcro® closures. Other embodiments are also within the scope of the invention. For example, pad 32 is portable, and can also be used by a patient in a more horizontally-oriented position, such as in a reclining chair. Pad 32 may also be placed on other suitable surfaces such as, for example, a table, bed, or sofa. Positions for treating patients placed with their backs at angles ranging from fifteen (15°) degrees in the forward position to forty five (45°) degrees in the backward or reclining position are especially advantageous in treating patients.

At least one transducer coil designated 104s is disposed in first portion or seat portion 36 of pad 32. Similarly, at least one transducer coil designated 104b is disposed in second portion or back portion 38 of pad 32. Bone mineral density stimulator 30 is preferably designed to treat the proximal femur, hip joint, lumbar and thoracic spine of female patients, ranging from the $5^{th}$ to $95^{th}$ percentile in size.

It is also within the scope of the invention for a plurality of transducer coils 104s or 104b (not expressly shown) that are operated by control unit 50 to be disposed in each of first portion 36 and second portion 38 of pad 32. For example, back portion 38 of pad 32 may dispose a plurality of transducer coils 104b oriented vertically, to treat the spine area. Additional transducer coils may also be configured to treat other portions of a patient's body such as wrists or ankles or other soft tissue areas for which such treatment is desirable. Construction of pad 32 and transducer coils 104s and 104b are discussed in further detail in conjunction with FIGS. 2 and 3.

Control unit or housing 50 as used in this embodiment is shown resting on table 26 in FIG. 1A. Flexible cable 52 is provided to electrically connect housing 50 with transducer coils 104s and 104b. For some applications, quick disconnect 54 may be provided in cable 52 between housing 50 and pad 32. Other suitable means for electronically connecting housing 50 to pad 32 may also be used.

Control unit 50 of bone mineral density stimulator 30 preferably sends programmed electrical impulses to transducer coils 104b and 104s disposed in pad 32. Transducer coils 104b and 104s, in turn, develop a pulsed electromagnetic field. Thus, when the patient is seated on pad 32, transducer coils 104b and 104s deliver a non-invasive, low-energy, pulsed electromagnetic field (PEMF) to a selected treatment site or sites of the patient.

The configuration of transducer coils 104s and 104b along with electrical drive signals provided by control unit 50 through flexible cable 52 are preferably selected to provide a relatively uniform magnetic field and relatively constant peak flux densities throughout a desired treatment volume.

Figure 9:
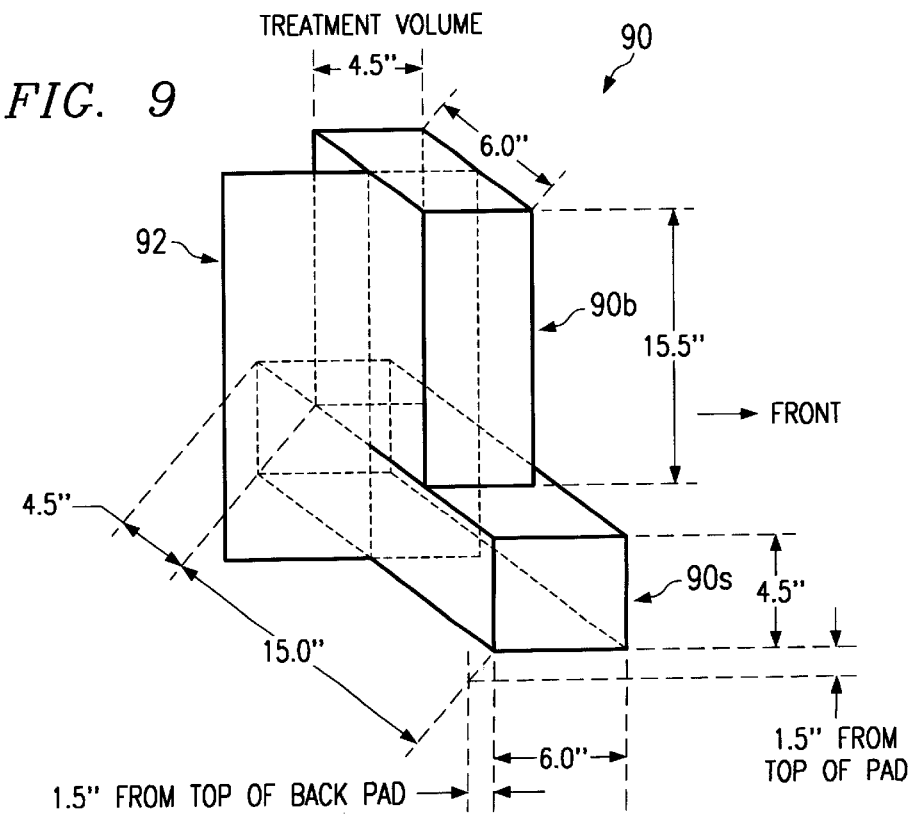
FIG. 9 is a schematic drawing showing approximate treatment volume provided by a bone mineral density stimulator such as shown in FIG. 1A.

One example of a treatment volume is discussed in further detail in conjunction with FIG. 9.

Control unit 50 will typically have an ON/OFF switch 56 which controls the operation of both transducer coils 104s and 104b. For some applications, two separate ON/OFF switches 56 and 58 may be provided to allow individually controlling transducer coils 104s and 104b. In this embodiment, control unit 50 also includes an additional switch (not explicitly shown) for controlling treatment information access. For one application, control unit 50 may have dimensions of approximately three and one-half inches (3.5") by five and one quarter inches (5.25") by one inch (1").

A number of indicator lights 60 may also be provided on control unit 50 to indicate operational status such as when treatment is in process, when treatment has been completed if a battery power source is low. Indicator lights 60 may comprise light emitting diodes (LEDs) that are easily visible in normal room lighting, from a distance of about three (3') feet. In this embodiment, control unit 50 includes color-coded LEDs, whose functions are described below and in conjunction with Table I. Other embodiments may include an audio transducer to provide an audible alarm function, in addition to, or instead of indicator lights 60. For some applications, an audio beep or buzzer may be defined as one second of sound followed by one second of silence.

For some applications, control unit 50 will contain a single nine (9) volt disposable lithium battery (not expressly shown). The battery is disposed within control unit 50 and accessible through a door (not explicitly shown) for replacement. Control unit 50 may be powered by any suitable battery or other standard power source.

Control unit 50 is preferably operable to detect whether the battery is low. While the unit is ON, if a low battery condition is detected, treatment is terminated and the red LED will flash to indicate that battery replacement is required. Similarly, when the unit is ON, if the battery voltage drops below a battery shutdown threshold, control unit 50 will automatically turn OFF.

In operation, to begin treatment, a patient may depress ON/OFF switch 56 once. The green LED will flash during normal treatment, which in this embodiment last for a time of between two and eight hours. It is often particularly advantageous for the patient to use bone mineral density stimulator 30 for a continuing treatment time of four hours. To terminate treatment prior to device time out, the patient may depress ON/OFF switch 56 again.

Table I lists visual and audio indications for one embodiment of the invention. For example, when a flashing LED alarm indication is activated, the LED flashes at a rate of approximately once per second. Normal Treatment in progress is indicated by a green LED continuously flashing at approximately once per second.

In operation, bone mineral density stimulator 30 will preferably provide a preset amount of daily treatment. Control unit 50 is operable to turn itself off at the end of the preset amount of treatment in a day. Prior to turning itself OFF, control unit 50 will preferably beep for five seconds and flash the yellow LED five times. The patient will be notified by a continuous audible alert and a steady red LED should a field fault occur while treatment is in progress (see Table I). Field fault sensing circuitry is discussed in further detail in conjunction with FIGS. 4 and 6.

TABLE I

Bone Mineral Density Stimulator: Visual & Audio Indicators

| Indication | Meaning |
|---|---|
| PATIENT MODE | |
| All LEDs and Continuous Audible Alert for ~3 secs. | Power-CN Self Test (POST) |
| Steady Yellow LED and Continuous Audible Alert | Power-ON Self Test Error |
| Flashing Green LED | Normal Treatment in Progress |
| Beep for 5 seconds and Green LED extinguished | Treatment Time Completed |
| Flashing Yellow LED | Treatment for the Day Completed |
| Flashing Red LED and Continued Audible Alert | Battery Replacement Required |
| Steady Red LED and Continuous Audible Alert | Service required/Field fault |
| COMPLIANCE DATA MANAGMENT MODE | |
| Green LED | Patient compliant since short term memory last cleared |
| Red LED | Patient has not been compliant since short. term memory last cleared |
| Beep 3 times | Compliance memory about to clear |

Control unit 50 is preferably operable to execute a system integrity or power on self test (POST) during the power-up sequence. This test may check the following parameters: Real time clock (RTC), Software and Memory Check sums. During this test, all LEDs and the buzzer turn on for approximately 3 seconds and then turn off. If this test fails, the patient may not start treatment. The yellow LED is lit, and an audio alarm may be sounded and remain on until control unit 50 is turned OFF.

Bone mineral density stimulator 30 is operable to maintain patient compliance history on a daily and cumulative basis by tracking treatment time. For example, in one embodiment, control unit 50 may accumulate treatment time for the current day following the first fifteen minutes of treatment. Control unit 50 is preferably operable to track treatment time in five-minute increments up to 900 minutes (15 hours) total, with a minimum treatment time for accumulation of one (1) hour. Control unit 50 can track treatment duration for up to four (4) treatment sessions in one day.

Control unit 50 is operable to retain the date of the first treatment day after shipment, defined as the first day control unit 50 is "ON" greater than one hour continuously. Similarly, control unit 50 is operable to determine from the calendar the quantity of total days and total hours of treatment since last clear.

Control unit 50 utilizes a Real Time Clock 404 with a battery to provide standby power during battery changes to perform time tracking. For one embodiment, control unit 50 is operable to store at least 117 days of patient usage information in a battery-backed data random access memory (RAM) 403. Details for a preferred embodiment of the electrical circuitry in control unit 50 are discussed in conjunction with FIG. 4.

Control unit 50 disposes a hidden switch (not explicitly shown) that may be used by a physician to enter into Compliance Data Management Mode as indicated in Table I. In this embodiment, Compliance Data Management Mode is accessed by depressing ON/OFF switch 56 and a logo switch (not explicitly shown) simultaneously and holding for three seconds. Exiting the Compliance Data Management Mode is performed by depressing ON/OFF switch 56 to power down control unit 50. Depressing the logo switch and holding for five seconds clears compliance memory 403.

Figure 4:
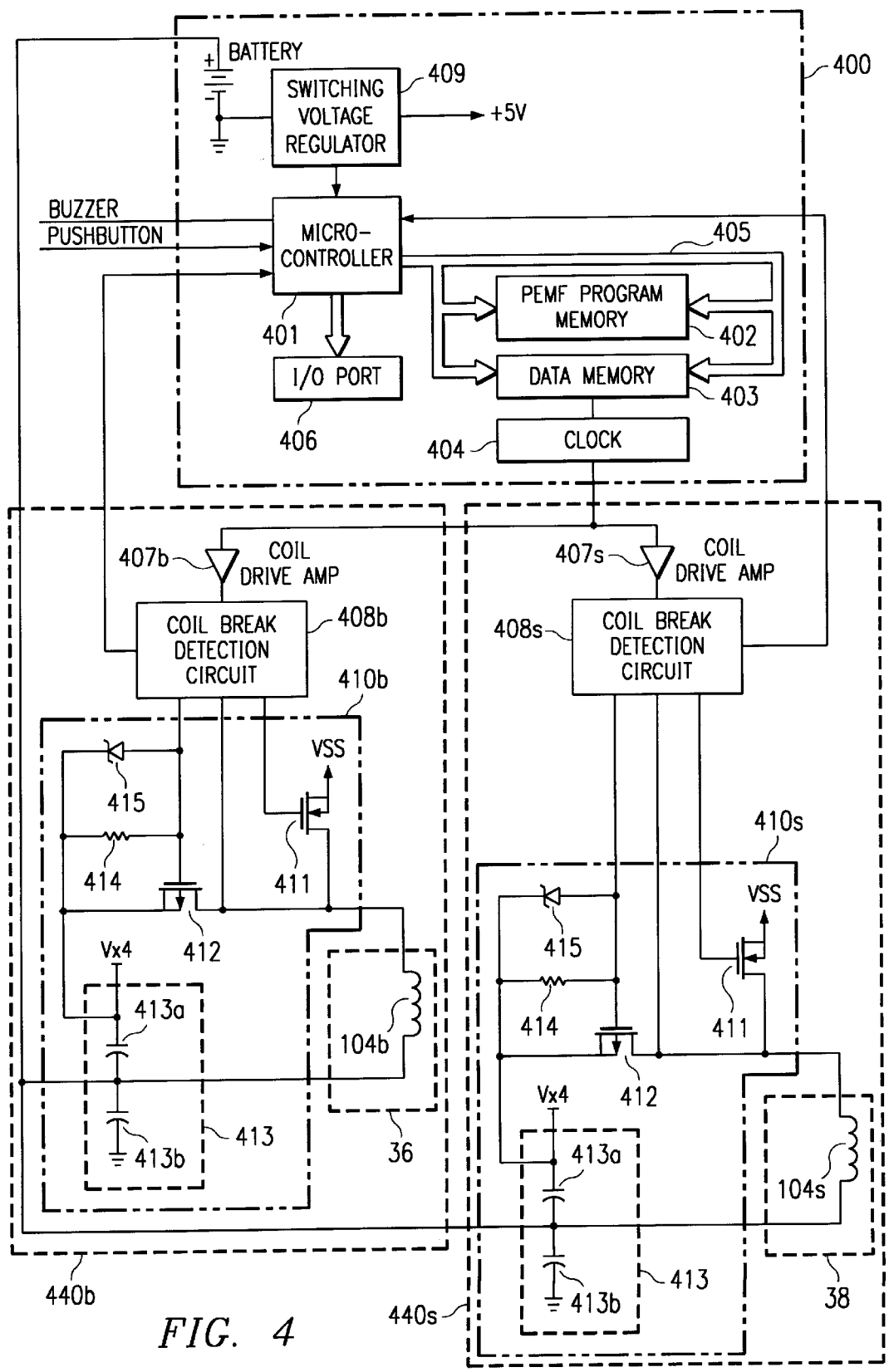
FIG. 4 is a schematic drawing of a block diagram of an electronic circuit and the transducer coils satisfactory for use with the bone mineral density stimulator shown in FIG. 1.

Control unit 50 provides a print mode of operation which enables the physician to request a printout of compliance data such as those indicated in Table II at any time during patient treatment. The print mode is initiated by pressing the logo switch on control unit 50 with a printer (not explicitly shown) attached. A compliance history is printed from the first treatment date. The print mode downloads the data indicated by an "*" in Table II from control unit 50 via a SIO port 406 as shown in FIG. 4 to any suitable external printer.

TABLE II

Patient Data

*Date of Printout
*Device Ser. No.
*Patient Name (OPTIONAL)
*Patient Identification Number (OPTIONAL)
*Doctor's Name (OPTIONAL)
Date of First Use
*Total Treatment Days Since Last Clear
Total Pre-set Treatment Days
Time of Last Clear
*Calendar of Daily Usage

*Printed data

Figure 1B:
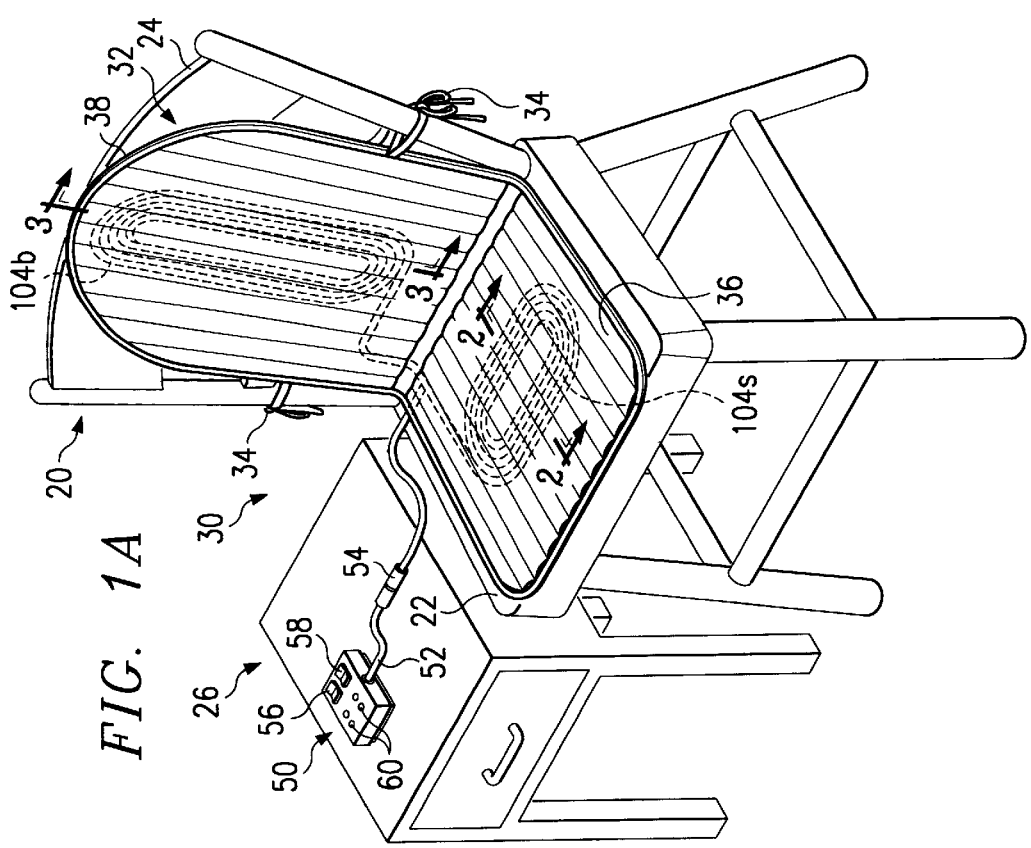
FIG. 1B is a schematic drawing showing a second isometric view of a bone mineral density stimulator incorporating teachings of the present invention disposed on a chair for treatment of a patient with electromagnetic therapy.

Another embodiment for bone mineral density stimulator 30 incorporating teachings of the present invention is shown in FIG. 1B secured to chair 20. In this embodiment, bone mineral density stimulator 30 includes pads 31 and 35, in addition to the elements as shown and discussed in conjunction with FIG. 1A. Bone mineral density stimulator 30 is preferably designed to treat the upper and lower extremities of a patient, in addition to the proximal femur, hip joint, lumbar and thoracic spine areas. In this embodiment, pad 31 is shown resting on chair 20, and pad 35 is shown resting on the floor. Pad 31 is preferably designed to treat upper extremities of a patient, such as wrists or arms. Pad 35 may be used to treat lower extremities of a patient, such as ankles or legs. Pads 31 and 35 need not rest on the floor, or be secured to chair 20. It is within the scope of the invention for additional pads 31 and 35 to be used to treat another upper or lower extremity, respectively.

At least one transducer coil designated 104a is disposed in pad 31. Similarly, at least one transducer coil designated 104l is disposed in pad 35. Each transducer 104s and 104l are operated by control unit 50. It is also within the scope of the invention for a plurality of transducer coils 104a or 104l (not expressly shown) that are also operated by control unit 50 to be disposed in each of pads 31 and 35. For example, pad 31 may dispose a plurality of transducer coils 104a oriented along its longitudinal axis, to treat both the patient's wrist and forearm. Construction of transducer coils 104a and 104l is identical to construction of transducer coils 104s and 104b, and is discussed in further detail in conjunction with FIGS. 2 and 3.

Flexible cables 52a and 52l are provided to electrically connect control unit 50 with transducer coils 104a and 104l, respectively. For some applications, quick disconnects 54a and 54l may be provided in cables 52a and 52l, respectively, between control unit 50 and pads 31 and 35. Other suitable means for electronically connecting control unit 50 to pads 31 and 35 may also be used. For example, a junction (not explicitly shown) may be provided at quick disconnect 54 to route additional cables 52a and 52l to control unit 50. Further, such a junction could also be placed near pad 36, which may minimize the lengths of cables 52a and 52l, and reduce potential tangling of the cables.

As discussed in conjunction with FIG. 1A, control unit 50 preferably sends programmed electrical impulses to transducer coils 104a and 104l disposed in pads 31 and 35. Transducer coils 104a and 104l, in turn, develop a pulsed electromagnetic field. Thus, when the patient is seated on pad 32, transducer coils 104a and 104l deliver a non-invasive, low-energy, pulsed electromagnetic field (PEMF) to a selected treatment site or sites of the patient.

The configuration of transducer coils 104a and 104l, along with electrical drive signals provided by control unit 50 through flexible cables 52a and 52l, are preferably selected to provide a relatively uniform magnetic field and relatively constant peak flux densities throughout a desired treatment volume.

Operation of control unit 50, and the typical accompanying visual and audio indications for this embodiment of the invention are similar to those discussed in conjunction with FIG. 1A. ON/OFF switch 56 located on control unit 50 also controls the operation of transducer coils 104a and 104l, in addition to transducer coils 104s and 104b. Bone mineral density stimulator 30 is also operable to execute system integrity tests and to maintain patient compliance history, both of which are discussed in conjunction with FIG. 1A.

Figure 1C:
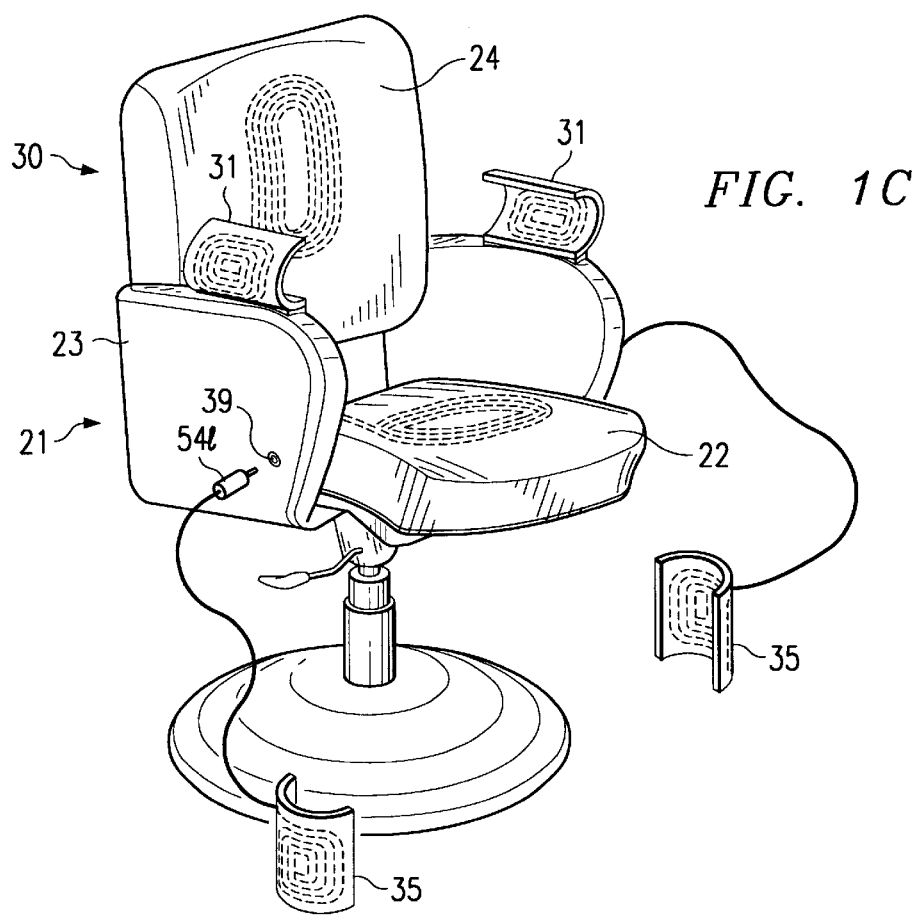
FIG. 1C is a schematic drawing showing an isometric view of a bone mineral density stimulator incorporating teachings of the present invention disposed within in a chair for treatment of a patient with electromagnetic therapy.

Pads 31 and 35 in this embodiment are generally c-shaped, in order to generally conform to a patient's upper or lower extremity, respectively. In this embodiment, pads 31 and 35 are each shown with a strap 31a and 35a that secures using Velcro®. Such a strap permits a patient to releasably conform pads 31 and 35 to, for example, his wrists and ankles. Other suitable means for conforming pads 31 and 35 to upper and lower extremities may also be used. For example, in one embodiment, pads 31 and 35 may be constructed by using suitable materials such that no straps or securing means are necessary. Such an embodiment is illustrated in FIG. 1C. Such materials are appropriate for contact with a patient's body, and include any hard resinous material, which may be elongated or compressed to more snugly fit the patient's extremity.

Pads 31 and 35 may also be constructed to various sizes, and may be interchangeable for the upper and lower extremities for some patients. Further, pads 31 and 35 may also be generally flat, of any suitable shape, and may generally also be constructed similarly to pads 36 and 38, as discussed in conjunction with FIGS. 2 and 3.

For some applications, pads 31 and 35 may also include an additional outer layer, not explicitly shown in FIG. 2, formed from a molded plastic. Such a plastic may be a thermoplastic polymer such as ABS, which may be elongated or compressed so that it can adapt to snugly fit pads 31 and 35 to a wide range of ankle or wrist sizes.

Another embodiment for bone mineral density stimulator 30 incorporating teachings of the present invention is shown in FIG. 1C disposed within chair 21. For this embodiment of the invention, transducer coils 104s and 104b are disposed within seat 22 and back 24 of chair 21, respectively. Bone mineral density stimulator 30 may be disposed within any suitable chair 21. For example, such a chair may be operable to recline, and/or include a vertical adjustment for seat portion 22. Pads 31 and 35 are illustrated in FIG. 1C as resting on chair 21 and the floor, respectively. It is also within the scope of the invention for pads 31 and 35 to be disposed within chair 21. For example, pads 31 may be disposed within side arm 23, and/or pads 35 may be disposed within an extended reclining leg portion (not explicitly shown) of a suitable chair 21.

Control unit 50 and cable 52 (not explicitly shown) may be located as shown in FIGS. 1A and 1B, on table 26, or disposed within chair 21. In this embodiment, cable 52 may be any suitable material for use within chair 21. For example, control unit 50 may be disposed within side arm 23 of chair 21, at a location convenient for the patient to operate. Control unit 50 and its operations are discussed in further detail in conjunction with FIG. 1A.

Bone mineral density stimulator 30 is preferably designed to treat the upper and lower extremities of a patient, in addition to the proximal femur, hip joint, lumbar and thoracic spine areas. Thus, bone mineral density stimulator 30 may operate in this embodiment with or without additional pads 31 and 35, to suit the patient's needs. In this embodiment, bone mineral density stimulator 30 includes four pads 31 and 35, for treatment of each upper and lower extremity. In this embodiment, cable 541 releasably engages with receptacle 39. Receptacle 39 is electrically coupled to control unit 50 (not explicitly shown). It is also within the scope of the invention for cable 541 to directly couple to cable 521, a receptacle, or quick release located on control unit 50.

Similarly, pad 31 may be electrically coupled to control unit 50 by many suitable means not explicitly shown. For example, an additional cable 54a may be releasably engaged with another receptacle 39, which may be placed directly under pad 31. Such a receptacle is electronically coupled to control unit 50, or to a suitably located junction.

FIGS. 2 and 3 are schematic drawings showing cross sectional views of transducer coils 104s and 104b formed in accordance with teachings of the present invention. Transducer coils 104s and 104b preferably have a substantially flat cross sectional profile which is a result of a flat wound construction. Transducer coils 104s and 104b preferably include a single set of primary windings. Transducer coils 104s and 104b may also include two or more primary windings in parallel layered on top of each other. Transducer coils 104s and 104b may be formed from commercially available eighteen gauge wire. In one embodiment, transducer coils 104s and 104b are wound according to the winding schedule: 1 layer×5 turns×20 American Wire Gauge (AWG). In this embodiment, transducer coils 104s and 104b each have a resistance of 0.32 ohms and an inductance of 25.4 $\mu$H.

For some applications, control unit 50 may be powered by a standard power source such as a wall unit. In this embodiment, transducer coils 104s and 104b may be wound according to a different winding schedule, for example, 2 layers×7 turns×20 AWG.

For some applications, pads 31, 32 and 35 preferably include outer layers 40 and 42 formed from flexible, durable material appropriate for contact with a patient's body. Layers 40 and 42 may be formed from vinyl and similar types of plastics. Pads 31, 32, and 35 preferably contain two or more elastomeric foam layers 44 and 46 with transducer coils 104s and 104b sandwiched therebetween. Various types of commercially available elastomeric materials may be used to form foam layers 44 and 46. Other embodiments are also within the scope of the invention. For example, transducer coils 104a, 104l, 104b and 104s may also be disposed within a single elastomeric foam layer 46. Furthermore, transducer coils 104a and 104l may also be disposed within other suitable materials.

For some applications, second portion or back portion 38 of pad 32 may include layer 48 formed from a sheet of polymeric material which may be deformed to assume various configurations. Layer 48 is preferably formed from material which may be easily manipulated to conform with the general configuration of a patient's back and to retain this configuration. Layer 48 may also provide support or stiffness for back portion of pad 32.

For some applications, layer 48 may be formed from synthetic resinous materials supplied by Kleerdex Company located in Bristol, Pa. and sold under the trademark KYDEX®.

FIG. 4 is a partly schematic and partly block diagram of one electrical circuit formed in accordance with teachings of the present invention. In the example of FIG. 4, this circuitry provides a pulsing bi-phasic current to transducer coils 104s and 104b at predetermined intervals, thereby activating the PEMF output signal according to a prescribed pre-programmed PEMF regimen. Except for transducer coils 104s and 104b, this circuitry may be physically located in control unit 50. The electrical circuitry includes both control circuitry 400, field sense circuitry 408 and drive circuitry 410, which all may be fabricated on a printed circuit board and encapsulated in control unit 50. In this embodiment, control circuitry 400 is operable to drive group circuitry 440s and 440b.

Control circuitry 400 includes processor or microcontroller 401, with associated integrated circuit components: a program memory 402, a data memory 403, and Real Time Clock circuit 404. For some applications, processor 401 may represent two individual microprocessors. One microprocessor may be used to control transducer coil 104s and the other microprocessor may be used to control transducer coil 104b.

Processor 401 is in data communication with these associated components by means of a bus 405. A PEMF program can be loaded into a microcontroller EPROM or other memory and installed as PEMF program memory 402. Alternatively, the PEMF program can be read into the PEMF program memory via I/O port 406.

Data memory 403 may be used to store data about the patient's use of bone mineral density stimulator 30, based on an internally maintained clock and calendar provided by clock circuit 404. For example, PEMF program parameters—such as start time, stop time, duration, and daily average—may be stored in data memory 403. This data can be read out or uploaded to any suitable printer, external device or communications link via the I/O port 406. In this embodiment, I/O port 406 is a recessed Serial Input/Output (SIO) port for connecting to such an external device.

Processor 401 controls coil drive amplifier 407, which drives the energization and de-energization of transducer coils 104s and 104b. Field sensor or coil break detection circuits 408s and 408b sense the electromagnetic fields output by respective transducer coils 104s and 104b and provide a response signal to processor 401 for monitoring the operation of bone mineral density stimulator 30. This built-in monitoring circuitry will ensure that the treatment field is being generated by proper current flow in each transducer coil 104b and 104s.

Processor 401 may store monitoring data in data memory 403, and will initiate a visible or audible warning signal or other alarm if the device is not generating the treatment field. If at any time during treatment either transducer 104b, 104s ceases to function properly, treatment will stop and the field fault indication is initiated.

In operation, processor 401 receives power from a power source, such as a nine-volt lithium or alkaline battery, through a switching voltage regulator 409. Regulator 409 provides +5 volts power to processor 401 and its associated digital components.

Processor 401 and its associated components may be implemented with conventional integrated circuit devices.

For example, processor 401 may be a Motorola 68HC11 processor. The data memory 403 and clock circuit 404 may be a Dallas Semiconductor Corporation device.

As explained further below in connection with FIGS. 7, 8, 10A, 10B and 10C, the PEMF program preferably outputs a pair of control signals, each comprising a series of pulse bursts. The two signals have their pulses offset, such that a pulse of one signal is high when a pulse of the other signal is low. These alternating control signals control the drive electronics so that it switches current on and off at the proper times to provide bi-phasic current for transducer coils 104s and 104b.

A feature of the control signals is that at the beginning of one of the pulse bursts, its first pulse is shorter than the other pulses in the same pulse train. Thus, for example, if the first pulse train has pulses with 4 microseconds (4 $\mu$sec) on and 12 microseconds (12 $\mu$sec) off times, then the first pulse of the first pulse train is 2 microseconds (2 $\mu$sec). This first short pulse sets up the magnetic field for the PEMF stimulation therapy signal in the single-winding coil. By turning on the drive circuitry for one-half pulse, energization of the magnetic field takes place to set the PEMF magnetic field away from zero. Then, the next pulse on the other pulse train turns on for approximately twelve microseconds. This sets the current so that the drive flyback energy goes in a negative direction. This causes current to flow from an initial negative direction. The current then ramps up through zero and increases from a negative number through zero to a positive number during the pulse.

Drive electronics 410s and 410b drive respective transducer coils 104s and 104b, so that transducer coils 104s and 104b then generate the desired PEMF stimulation therapy signals. Drive electronics 410s and 410b have a first transistor switch 411 between break detection circuit 408 and transducer coils 104s and 104b, and a second transistor switch 412 between energy recovery capacitance circuit 413 and transducer coils 104s and 104b. Switches 411 and 412 control the output signal from transducer coils 104s and 104b. In operation, each transducer coil 104s and 104b shapes the pulsed electromagnetic field pattern and recovers unused energy during the interpulse collapse of the generated field.

For initialization, switch 411 is turned on by coil drive amplifier 407 to present battery voltage across transducer coils 104s and 104b for a period of one-half a normal pulse duration of typically four microseconds (4 $\mu$sec). Activation current flows through transducer coils 104s and 104b to generate an output signal. When switch 411 switches off, switch 412 switches on to charge energy recovery capacitance circuit 413 to a voltage equal to four times the battery voltage. This causes transducer coils 104s and 104b to discharge in the opposite direction during the off period of switch 411 as compared to the direction during its on period. Thus, energy recovery occurs without a secondary coil. Drive circuits 410s and 410b permit sequencing of the current through respective transducer coils 104s and 104b in both directions.

Therefore, for a given magnetic field strength, the peak current can be cut in half. This results in a factor of four reduction in $I^2R$ losses, where I is the instantaneous coil current and R is the resistance of the coil winding. These are the types of losses that would exist with the use of a secondary winding. The voltage $V_{x4}$ may be derived using the flyback pulse from transducer coils 104s and 104b, instead of requiring a separate voltage boost circuit. By balancing the capacity of capacitors 413a and 413b, it is possible to eliminate the need for a separate four-times voltage supply circuit.

In the example of FIG. 4, energy recovery capacitance circuit 413 comprises two series connected capacitors 413a and 413b. Their capacitance ratio is at least 1:3, and in the example of this description is 1:10 (in microfarads). Various other capacitor configurations could be used for capacitance circuit 413, with the common characteristic that it provides the desired energy restoring voltage, here $V_{x4}$. For example, energy recovery capacitance circuit 413 could comprise a capacitor and voltage regulator circuitry.

Control circuitry 400 is also operable to drive additional group circuitry such as circuitry 440a and circuitry 440l (not explicitly shown). Such additional group circuitry may be placed in parallel with group circuitry 440s and 440b without substantively altering the load on control circuitry 400. Thus, a number of additional bone mineral density stimulator devices such as wrist and ankle transducer coils 104a and 104l may be releasably coupled to control circuitry 400, and operated in conjunction with transducer coils 104s and 104b. Such configurations are shown in FIGS. 1B and 1C.

FIG. 5 illustrates an example of an output waveform generated by transducer coils 104s and 104b. A pulse portion I is followed by pulse portion II. Pulse portion I has a duration of approximately four microseconds (4 $\mu$sec). Pulse portion II has a duration of approximately twelve microseconds (12 $\mu$sec). The voltage level for pulse portion I is approximately three times the voltage level for portion II. The areas of the portions I and II, therefore, are approximately equivalent. The output pulse periods (16 microseconds) and pulse frequency (62.5 kilohertz) of the output signal are in response to the pulsed drive signals. The output waveform is discussed in further detail in conjunction with FIGS. 8, 10A, 10B, and 10C.

FIG. 6 illustrates one embodiment of coil break detection circuit 408. A set/reset flip-flop 61 receives an upper input signal and a lower input signal. One of its Q outputs goes to flip-flop 62 and controls the operation of switch 412. The other Q output controls the operation of switch 411. The Q output from flip-flop 62 goes to flip-flop 63 as a clock signal. Switch 412 controls whether the COIL_LO signal goes to $V_{x4}$, while switch 411 shunts COIL_LO to ground. The COIL_HI signal provides supply voltage V.

Resistor 64 and diode 65 receive supply voltage, V, from resistor 66. Flip-flop 63 receives as its D input the output from resister 66. The Q output from flip-flop 63 goes to NAND gate 67 to generate a sense output.

Figure 7:
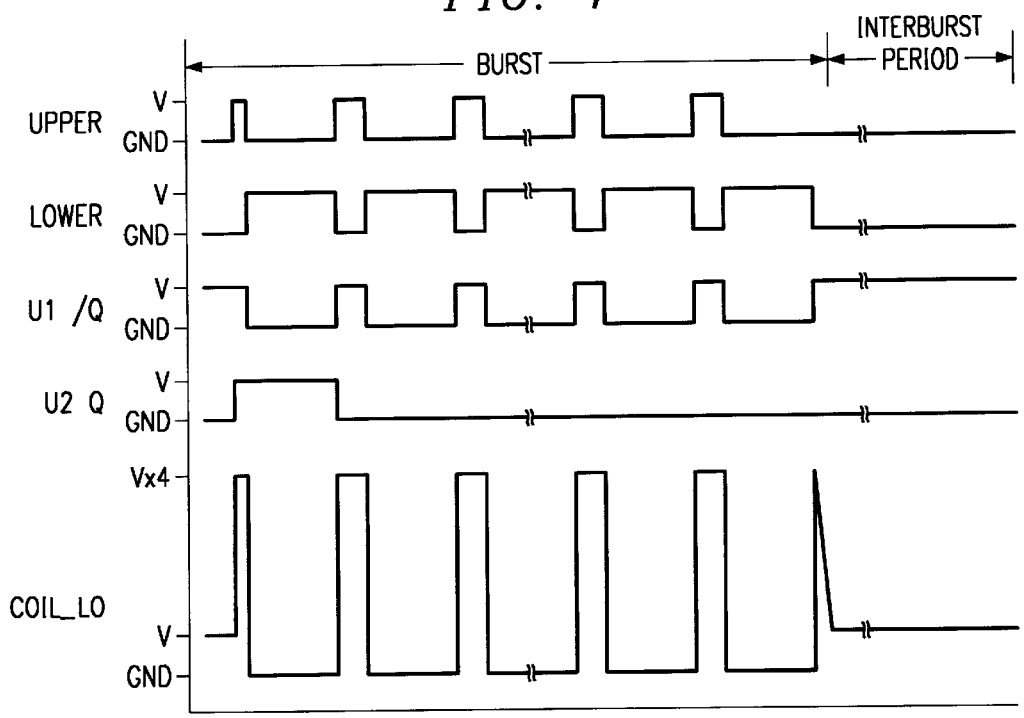
FIG. 7 is a drawing which illustrates the input logic versus signal provided to the transducer drive circuit shown in FIG. 4.

The voltage $V_{x4}$ is four times the voltage V, both being measured with respect to ground. The UPPER and LOWER signals consist of a burst of pulses, separated by an inter-burst period, as shown in FIG. 7. These two signals are essentially non-overlapping ensuring the stable operation of the S/R flip-flop 61. The Q outputs of S/R flip-flop 61 are of opposite state and are also essentially non-overlapping, ensuring that switches 411 and 412 are never simultaneously on.

During the inter-burst period, both switches 411 and 412 are open. Under normal operating conditions, transducer coils 104s and 104b will pull the COIL_LO signal level to the supply voltage V. If a break should occur in the coil, the COIL_LO signal will be pulled to ground by resistor 64.

Resistor 66, resistor 64, and diode 65 translate the COIL_LO signal to levels appropriate for the inputs of flip-flop 63 and NAND gate 67. The ratio of resistor 66 to resistor 64 is selected to provide a logic level "0" at the inputs of flip-flip 63 and NAND gate 67 should a break occur in transducer coils 104s and 104b.

The output of flip-flop 62 is a single pulse occurring at the beginning of a burst, beginning with the first pulse of UPPER and terminating on the second pulse of UPPER. The rising edge of the output of flip-flop 62 occurs prior to the first rising edge of COIL_LO due to the relatively short time delay associated with flip-flop 62 versus switch 412 and switch 411. The pulse output of flip-flop 62 goes to flip-flop 63, samples the inter-burst voltage. If the inter-burst voltage is equal to V, the Q output of flip-flop 63 is a logic level "1" until the next sampling pulse, thereby enabling output of the inverse of the COIL_LO signal to processor 401 as the SENSE signal.

If the inter-burst voltage is at a ground level, due to a break in the transducer coils 104s and 104b, the output of flip-flop 63 is set to a logic level "0", disabling the output of the inverse of the COIL_LO signal to processor 401.

A short across the coil terminals will cause the COIL_LO signal to be tied to V. The output of flip-flop 63 will be a logic level "1," therefore the output of NAND gate 67 will be a logical level "0" rather than the burst signal that processor 401 normally expects. This indicates the existence of a field fault condition. Connecting either the COIL_HI or COIL_LO terminal to ground, will essentially create a DC short.

FIG. 7 illustrates the timing relationship of the logic signals that drive switches 411 and 412, as well as signals internal to coil break detection circuit 408. In each logic burst signal, there are a number of pulses, the duration of each upper pulse being only one-third the duration of lower pulse. Other parameters may also be used.

FIG. 8 is a table of parameters, requirements, units, and symbols that correspond to the timing diagram of FIG. 7. In the table of FIG. 8, the burst period is 26 milliseconds, during which a first pulse width is approximately two microseconds (2 μsec). Thereafter, the upper pulse width is approximately four microseconds (4 μsec). The lower pulse width is approximately twelve microseconds (12 μsec). The pulse period is approximately sixteen microseconds (16 μsec) for a pulse frequency of approximately 62.5 kilohertz. For the example of FIG. 8, there are 1609 pulses per burst. Such a combination of parameters is particularly advantageous in increasing energy efficiency, since the area of each transducer 104s, 104b may be large. These parameters reduce the operating requirements for battery power. The invention may also use other timing parameters to achieve the desired PEMF signals and associated energy recovery operation.

For the output PEMF signal described above, energy recovery capacitance circuit 413 provides an energy recovery voltage of four times the source voltage provided by the battery. As explained above, both the source voltage (V) and the energy recovery voltage ($V_{4\times}$) are lower than the voltages required for previous designs.

FIG. 9 is a schematic drawing showing an approximate treatment volume provided in the embodiment represented by bone mineral density stimulator 30 shown in FIG. 1A. Treatment volume 90 includes first portion 90s and second portion 90b. First portion 90s and second portion 90b correspond to the treatment site targeted by the embodiment of bone mineral density stimulator 30 as shown in FIG. 1A. Bone mineral density stimulator 30 preferably provides a uniform magnetic field and constant peak flux density throughout treatment volume 90. For the embodiment as shown in FIG. 1A, first portion 90s may have an approximate length of fifteen (15) inches, an approximate height of four and one half (4.5) inches, and an approximate depth of six (6) inches. Similarly, second portion 90b may have an length versus width approximate width of fifteen and one-half (15.5) inches, an approximate height of four and one-half (4.5) inches, and an approximate depth of six (6) inches. Treatment volume 90 is measured at an approximate distance of one and one-half (1.5) inches from both first portion 36 and second portion 38 of pad 32. In this embodiment, the length of first portion 90s extends approximately four and one-half (4.5) inches on either side of second portion 90b. This particular arrangement for first portion 90s and second portion 90b of treatment volume 90 is obtained as a result of the orientation, placement, and geometry of transducer coils 104s and 104b. Thus, the shape of treatment volume 90 depends on the particular arrangement, geometry, and orientation of transducer coils 104s and 104b.

It is particularly advantageous for a patient using bone mineral density stimulator 30 to be treated with a non-invasive uniform magnetic field and constant peak flux density throughout the volume of treatment site 90. The expected peak changes in flux density in this embodiment for bone mineral density stimulator 30 are discussed in conjunction with FIGS. 10B and 10C.

Similarly, bone mineral density stimulator 30 is operable to maintain a uniform magnetic field throughout treatment volume 90, as measured by magnetic field amplitude, intensity, and angle of divergence data as measured with respect to a plane perpendicular to the plane of symmetry, designated 92 in FIG. 9.

Figure 10A:
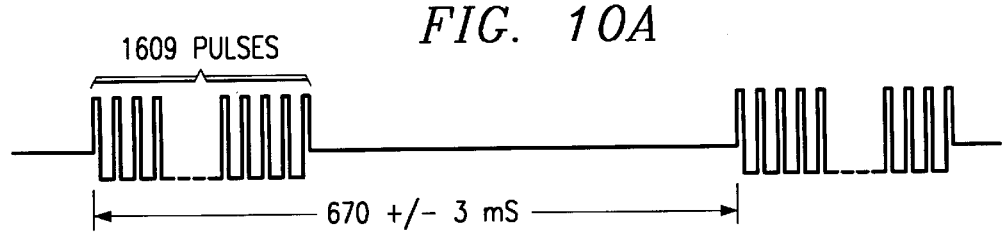
FIGS. 10A, 10B and 10C are drawings showing typical wave forms associated with a bone mineral density stimulator incorporating teachings of the present invention.
Figure 10B:
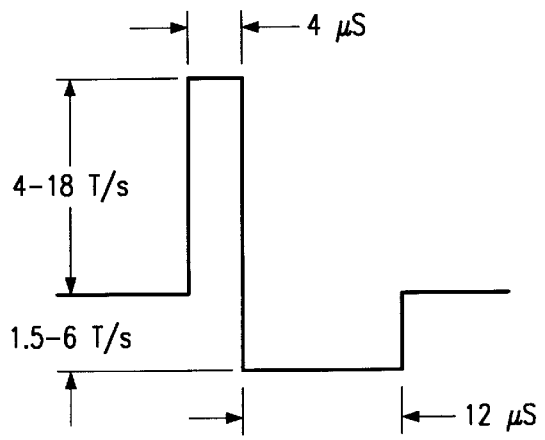
Figure 10C:
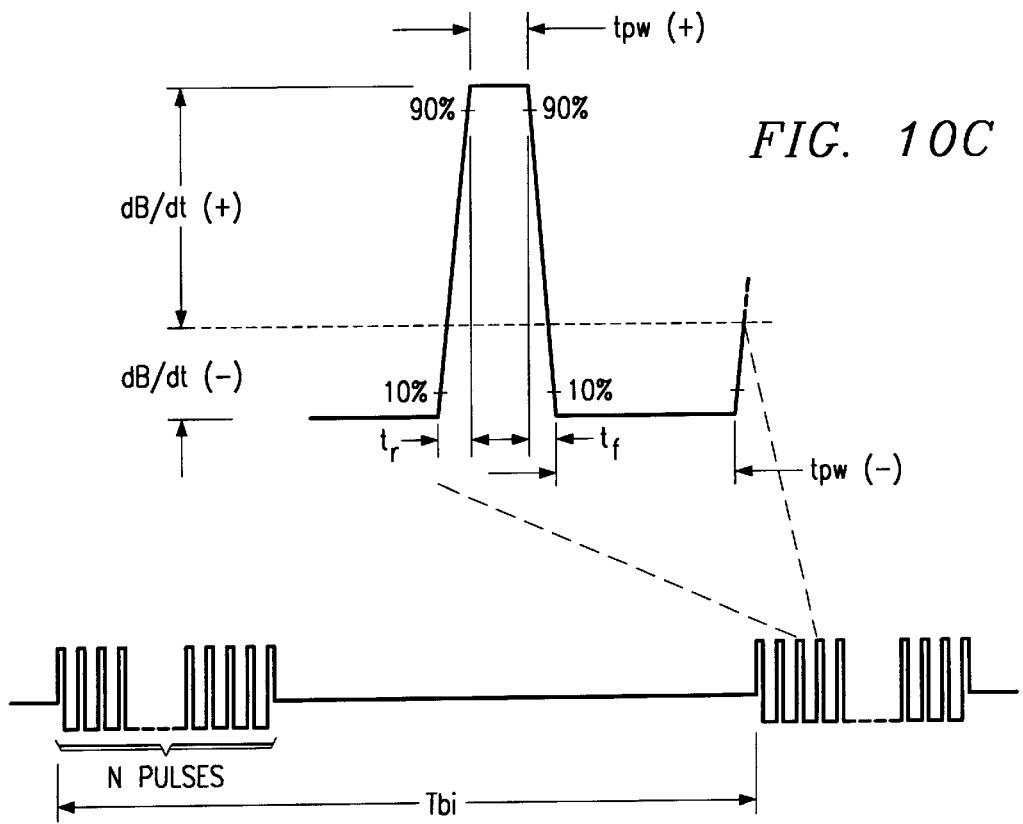

FIGS. 10A, 10B, and 10C are drawings showing typical wave forms associated with bone mineral density stimulator 30. In this embodiment, bone mineral density stimulator 30 delivers a burst of 1609 pulses during a burst period which are followed by an inter-burst period. Bone mineral density stimulator 30 delivers the burst at a rate of about one and a half pulse bursts per second, which corresponds to one burst approximately every 667+/−3 milliseconds (msec), as shown in FIG. 10A.

FIG. 10B illustrates the peak changes in flux density during the upper pulse width and the lower pulse width as shown in and discussed in conjunction with FIG. 5. The peak change in flux density during the upper pulse width is between four and eighteen T/s, also designated in units of dB/dt. Similarly, during the lower pulse width, the peak change in flux density is one and a half to six T/s.

FIG. 10C illustrates additional parameters associated with the wave form illustrated in FIG. 5, and shows the relationship of that wave form to the pulse burst as shown in FIG. 10A. Thus, each of the 1609 pulses as shown in FIG. 10A as used in this embodiment is associated with typical values for the parameters detailed in Table III. For example, the rise time, illustrated as $t_r$ in FIG. 10C and the fall time, as designated t in FIG. 10C are both one microsecond (1 μsec). Both the rise time and the fall time are measured by the amount of time it takes for the wave form to rise or fall respectively from ten percent (10%) to ninety percent (90%) of the voltage level between pulse portions I and II as illustrated in FIG. 5. Pulse portion I as illustrated in FIG. 5 is designated $t_{pw(+)}$, or on time, and lasts for four microseconds (4 μsec). Pulse portion II as illustrated in FIG. 5 is designated $t_{pw(-)}$, or off time, lasts for 12 microseconds (12 μsec). The peak flux density range in dB/dt for both pulse portion I and pulse portion II, is discussed previously in conjunction with FIG. 10B is shown here with respect to the wave form as illustrated in FIG. 10C.

Typical values for this waveform for a two-coil system as shown in FIG. 1A are presented below:

TABLE III

Bone Mineral Density
Stimulator Output Waveforms

| Parameter | Value |
|---|---|
| Current Drain | 30 mA max |
| Rise Time | 1 $\mu$S |
| Fall Time | 1 $\mu$S |
| On Time | 4 $\mu$S |
| Off Time | 12 $\mu$S |
| Burst | 1609 pulses |
| Burst Interval | 667 +/− 3 ms |

As more transducer coils M and N are added to bone mineral density stimulator 10, the current drain as illustrated in Table III will generally increase beyond the typical maximum 30 milliamps as shown for a two-coil system.

Although the present invention has been described in detail, it should be understood that various changes, substitutions and alterations can be made hereto without departing from the spirit and scope of the invention as defined by the appended claims.

What is claimed is:

1. An apparatus for providing electromagnetic therapy to a patient comprising:

a housing containing an electrical circuit for generating an electrical drive signal;

a first transducer coil and a second transducer coil for generating respective electromagnetic fields in response to the drive signal;

a first portion with a configuration corresponding generally with a chair seat and a second portion with a configuration corresponding generally with a chair back, the first transducer coil disposed within the first portion and the second transducer coil disposed within the second portion;

a flexible cable adapted to connect the electrical drive signal with the first transducer coil and the second transducer coil; and the first and second transducer coils being adapted to cooperate with each other to produce a pulsed electromagnetic field having a plurality of pulses in response to the electrical drive signal, each pulse having a pulse period of ten microseconds to twenty microseconds.

2. The apparatus of claim 1 wherein the first portion comprises a first pad and the second portion comprise a second pad, the first transducer coil disposed within the first pad and the second transducer coil disposed within the second pad.

3. The apparatus of claim 2 wherein the pad further comprises a layer of material which is conformable in response to pressure from the general shape of the patient's back and will retain the general shape when the pressure is released.

4. The apparatus of claim 3 wherein the second transducer coil having sufficient flexibility to conform with the general shape of the patient's back.

5. The apparatus of claim 2 wherein the pad further comprises an exterior layer of polyvinyl elastomeric material and at least one layer of flexible elastomeric foam material.

6. The apparatus of claim 1 further comprising:

an extremity pad having a portion with a configuration which is conformable generally to a patient's upper extremity;

at least one third transducer coil disposed within the extremity pad for generating electromagnetic fields in response to the drive signal; and a flexible cable adapted to connect the electrical drive signal with the third transducer coil.

7. The apparatus of claim 1 further comprising:

an extremity pad having a portion with a configuration which is conformable generally to a patient's lower extremity;

at least one third transducer coil disposed within the extremity pad for generating electromagnetic fields in response to the drive signal; and a flexible cable adapted to connect the electrical drive signal with the third transducer coil.

8. The apparatus of claim 1 further comprising:

a lower extremity pad having a portion with a configuration which is conformable generally to a patient's lower extremity;

at least one third transducer coil disposed within the lower extremity pad for generating electromagnetic fields in response to the drive signal;

an upper extremity pad having a portion with a configuration which is conformable generally to a patient's upper extremity;

at least one fourth transducer coil disposed within the upper extremity pad for generating electromagnetic fields in response to the drive signal; and at least one second flexible cable adapted to connect the electrical drive signal with the third transducer coil and the fourth transducer coil.

9. The apparatus of claim 1 wherein the electrical circuit further comprises a circuit for recovering flyback energy from the transducer coils and for sequencing current through the transducer coils in a positive direction and a negative direction.

10. The apparatus of claim 1 wherein the electrical circuit further comprises at least one processor operable to control the drive signal.

11. The apparatus of claim 1 further comprising a quick disconnect disposed in the flexible cable between the housing and the transducer coils.

12. The apparatus of claim 1 wherein the electrical circuit is further operable to monitor whether the respective electromagnetic fields are being properly generated by each of the first and second transducer coils.

13. The apparatus of claim 1 wherein the housing further comprises a battery for supplying electrical power to the electrical circuit.

14. The apparatus of claim 1 wherein the plurality of pulses is equal to approximately one thousand six hundred nine (1609).

15. The apparatus of claim 1 wherein the first portion comprises a chair seat and the second portion comprise a chair back.

16. The apparatus of claim 15 further comprising the housing disposed within the chair.

17. The apparatus of claim 15 further comprising the cable adapted to releasably connect to a receptacle in the chair.

18. The apparatus of claim 15 further comprising the chair operable to recline.

19. The apparatus of claim 1 further comprising :
at least one third transducer coil disposed within a lower extremity pad and at least one fourth transducer coil disposed within an upper extremity pad for generating respective electromagnetic fields in response to the drive signal; and
at least one additional cable adapted to connect the electrical chive signal with the third transducer coil and the fourth transducer coil.

20. A bone mineral density stimulator for treating a patient with electromagnetic therapy, comprising:
a first transducer coil and a second transducer coil;
a housing adapted to contain an electrical circuit for generating an electrical drive signal;
a cable adapted to connect the electrical drive signal with the first transducer coil and the second transducer coil, the first and second transducer coils adapted to generate respective electromagnetic fields in response to the electrical drive signal;
the first and second transducer coils being adapted to cooperate with each other to produce a pulsed electromagnetic field having a plurality of pulses in response to the electrical drive signal, each pulse having a pulse period of ten microseconds to twenty microseconds;
at least one extremity pad;
at least a third transducer coil disposed within the extremity pad; and
a cable adapted to connect the electrical drive signal with the third transducer coil, the third transducer coil adapted to generate an electromagnetic field extending from the extremity pad in response to the electrical drive signal.

21. The bone mineral density stimulator of claim 20 further comprising a pad formed from at least one layer of material, the pad having a first portion in which the first transducer coil is disposed and a second portion in which the second transducer coil is disposed.

22. The bone mineral density stimulator of claim 21 further comprising the first portion of the pad having a general configuration corresponding with a chair seat and the second portion of the pad having a general configuration corresponding with a chair back.

23. The bone mineral density stimulator of claim 21 further comprising the first portion of the pad flexibly coupled with the second portion of the pad.

24. The bone mineral density stimulator of claim 21 further comprising at least one strap attached to the second portion of the pad for releasably securing the pad with a chair back.

25. The bone mineral density stimulator claim 21 wherein the second portion of the pad further comprises a layer of material which is conformable in response to pressure from the general shape of the patient's back and will retain the general shape when the pressure is released.

26. The bone mineral density stimulator claim 21 wherein the layer of material comprises a layer formed from synthetic resinous material.

27. The bone mineral density stimulator claim 21 wherein the pad further comprises an exterior layer of polyvinyl elastomeric material and at least one layer of flexible elastomeric foam material.

28. The bone mineral density stimulator of claim 20 wherein the extremity pad has a portion with a configuration which is conformable generally to a patient's upper extremity.

29. The bone mineral density stimulator of claim 20 wherein the extremity pad has a portion with a configuration which is conformable generally to a patient's lower extremity.

30. The bone mineral density stimulator of claim 20 wherein the plurality of pulses have a pulse width of approximately sixteen microseconds.

* * * * *